(12) United States Patent
Richards

(10) Patent No.: US 8,939,918 B2
(45) Date of Patent: *Jan. 27, 2015

(54) CALIBRATION AND MEASUREMENT SYSTEM

(76) Inventor: Thomas J. Richards, Chino Hills, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 13/405,555

(22) Filed: Feb. 27, 2012

(65) Prior Publication Data

US 2012/0157883 A1    Jun. 21, 2012

Related U.S. Application Data

(63) Continuation of application No. 12/069,045, filed on Feb. 7, 2008, now Pat. No. 8,123,704.

(51) Int. Cl.
| | |
|---|---|
| A61B 5/103 | (2006.01) |
| A61B 5/117 | (2006.01) |
| G01B 3/00 | (2006.01) |
| G01B 3/14 | (2006.01) |
| B43L 13/20 | (2006.01) |
| B43L 7/00 | (2006.01) |

(Continued)

(52) U.S. Cl.
CPC ............... *A61B 5/107* (2013.01); *A61B 5/445* (2013.01); *A61B 5/0059* (2013.01); *A61B 5/6832* (2013.01)
USPC ............. 600/587; 600/588; 600/591; 33/501; 33/514.1; 33/562; 33/563; 33/565; 33/566

(58) Field of Classification Search
CPC ...... A61B 5/107; A61B 5/1072; A61B 5/441; A61B 5/445; G01B 3/02; G01B 3/10; G01B 3/34; G01B 3/1082; G01B 3/1083
USPC ............... 33/501, 514.1, 562, 563, 565, 566; 600/587, 588
See application file for complete search history.

(56) References Cited

U.S. PATENT DOCUMENTS 1,062,525 A * 5/1913 Ward ............................. 33/555.2
1,667,802 A * 5/1928 Homan, Jr. ...................... 33/3 A (Continued)

OTHER PUBLICATIONS

Colored Reinforcement Rings by Alibaba.com, Google Search, webpage made avaliable Nov. 4, 2005.*

(Continued)

*Primary Examiner* — Sean Dougherty
(74) *Attorney, Agent, or Firm* — Larry K. Roberts

(57) ABSTRACT

Embodiments of the present invention include a calibration and measurement system designed primarily for use in the rapid evaluation and characterization of open or visible wounds in patients. The invention in a preferred embodiment comprises a set of colored concentric rings, typically constructed of paper or synthetic paper. The practitioner removes only as many rings, from the center outward, until the entire wound is visible within the open aperture at the center of the remaining rings. The area dimensions of the wound are then read out from the size of the inner remaining ring. Photography optionally records the wound appearance and size. A related system is developed for linear dimensioning of wounds. This embodiment is also designed to standardize the color scheme for accurate photography wound description. The color scheme is also applicable to a linear device to accurately describe wound size. Embodiments of the invention are also useful in forensic and accident investigations.

19 Claims, 7 Drawing Sheets

(51) Int. Cl.
*A61B 5/107* (2006.01)
*A61B 5/00* (2006.01)

(56) References Cited

U.S. PATENT DOCUMENTS

| | | | |
|---|---|---|---|
| 2,049,245 A * | 7/1936 | Breitbarth | 33/1 B |
| 2,346,219 A * | 4/1944 | Johnson | 40/638 |
| 2,478,071 A * | 8/1949 | Agrillo | 33/565 |
| 2,500,873 A * | 3/1950 | Sager | 33/563 |
| 2,574,152 A * | 11/1951 | Lewis et al. | 428/41.7 |
| 4,131,998 A * | 1/1979 | Spears | 33/1 C |
| 4,219,029 A * | 8/1980 | Grossman et al. | 600/587 |
| D266,820 S * | 11/1982 | Ferrin | D10/46.3 |
| 4,389,782 A * | 6/1983 | Webster | 33/1 BB |
| 4,485,585 A * | 12/1984 | Shackelford et al. | 446/117 |
| 4,982,627 A * | 1/1991 | Johnson | 81/121.1 |
| 5,051,259 A * | 9/1991 | Olsen et al. | 424/443 |
| 5,106,629 A * | 4/1992 | Cartmell et al. | 424/445 |
| 5,264,218 A * | 11/1993 | Rogozinski | 424/445 |
| 5,265,605 A * | 11/1993 | Afflerbach | 600/300 |
| D348,618 S * | 7/1994 | Leslie et al. | D10/64 |
| 5,364,200 A * | 11/1994 | Russo et al. | 402/79 |
| 5,414,943 A * | 5/1995 | Vogt | 33/764 |
| 5,450,678 A * | 9/1995 | Check | 33/833 |
| 5,527,111 A * | 6/1996 | Lysen et al. | 374/208 |
| 5,577,328 A * | 11/1996 | Kerry, Sr. | 33/562 |
| 5,588,428 A * | 12/1996 | Smith et al. | 600/425 |
| 5,618,292 A * | 4/1997 | Poler | 606/166 |
| 5,619,804 A * | 4/1997 | Vogt et al. | 33/763 |
| 5,807,281 A * | 9/1998 | Welch | 600/588 |
| 5,884,408 A * | 3/1999 | Simmons | 33/494 |
| 5,967,979 A * | 10/1999 | Taylor et al. | 600/407 |
| 6,044,572 A * | 4/2000 | Sore et al. | 33/555.4 |
| 6,066,104 A * | 5/2000 | Dao et al. | 600/588 |
| 6,159,167 A * | 12/2000 | Hardin-Naser | 600/587 |
| 6,216,354 B1 * | 4/2001 | Carbone | 33/565 |
| 6,286,224 B1 * | 9/2001 | Lewis | 33/562 |
| 6,321,457 B1 * | 11/2001 | Lariviere et al. | 33/562 |
| 6,446,571 B1 * | 9/2002 | Sloot | 116/63 P |
| 6,489,760 B2 * | 12/2002 | Kim et al. | 324/207.18 |
| 6,609,309 B2 * | 8/2003 | Shibuya | 33/733 |
| 6,797,855 B2 * | 9/2004 | Worthley | 602/57 |
| D499,029 S * | 11/2004 | Maarberg | D10/46.3 |
| 6,820,478 B1 * | 11/2004 | Nabarro et al. | 73/149 |
| 6,893,422 B2 * | 5/2005 | Altman | 604/174 |
| 6,895,808 B2 * | 5/2005 | Remmlinger et al. | 73/53.07 |
| 6,917,895 B2 * | 7/2005 | Paanasalo | 702/157 |
| 7,150,108 B2 * | 12/2006 | Babb | 33/563 |
| 7,242,197 B2 * | 7/2007 | Satou et al. | 324/522 |
| 7,401,413 B1 * | 7/2008 | Nelson | 33/512 |
| 7,566,057 B2 * | 7/2009 | Mascolo | 273/153 P |
| D599,416 S * | 9/2009 | Turco-Rivas | D21/479 |
| 7,707,736 B2 * | 5/2010 | Keenan | 33/566 |
| 7,772,454 B2 * | 8/2010 | Addison et al. | 602/48 |
| 7,790,946 B2 * | 9/2010 | Mulligan | 602/57 |
| D634,009 S * | 3/2011 | Lam et al. | D24/140 |
| 8,009,884 B2 * | 8/2011 | Chio | 382/128 |
| 8,276,287 B2 * | 10/2012 | Estocado | 33/511 |
| 2001/0042982 A1 * | 11/2001 | McClure et al. | 283/81 |
| 2002/0115954 A1 * | 8/2002 | Worthley | 602/57 |
| 2003/0153860 A1 * | 8/2003 | Nielsen et al. | 602/43 |
| 2003/0219469 A1 * | 11/2003 | Johnson et al. | 424/445 |
| 2006/0058721 A1 * | 3/2006 | Lebner et al. | 602/42 |
| 2006/0100739 A1 * | 5/2006 | Raffle et al. | 700/245 |
| 2007/0066946 A1 * | 3/2007 | Haggstrom et al. | 604/313 |
| 2008/0008370 A1 * | 1/2008 | Chio | 382/128 |
| 2009/0084179 A1 * | 4/2009 | Gougian | 73/427 |
| 2009/0204028 A1 * | 8/2009 | Richards | 600/587 |
| 2013/0115848 A1 * | 5/2013 | Silverglate et al. | 446/124 |

OTHER PUBLICATIONS

Colored Reinforcement Rings by Alibaba.com, webpage made available Nov. 4, 2005.*

* cited by examiner

CALIBRATION AND MEASUREMENT SYSTEM

This application is a continuation of, and claims the benefit of, U.S. application Ser. No. 12/069,045 filed Feb. 7, 2008 now U.S. Pat. No. 8,123,704, the entire contents of which application is hereby incorporated by reference.

BACKGROUND

This invention relates generally to the field of wound calibration and measurement in hospitals and all other medical settings, and in forensic and accident investigations.

The treatment of wounds is often dependent upon rapid assessment of the nature of the wound. Size in terms of the area, or the length of the wound, is often critical. An accurate description and assessment of the measured wound allows for documentation of demonstrated healing and possibly reduce legal liabilities. Hospitals, nursing homes, home health care and military field hospitals are examples of assessing wound size initially and through the progression of the healing process of the wound. Furthermore, SB 1301 mandated all acute care hospitals to report stage 3 and stage 4 wounds to state licensing agencies. When these state agencies investigate the wound, accurate wound size is imperative to demonstrate healing.

U.S. Pat. No. 6,159,167 describes a disposable wound measuring assembly. This invention comprises a device that looks like a graduated glass cylinder on its side, complete with length markings, as on a ruler. The device includes an indicator ring that can be positioned along the length of the cylinder to mark the length of a wound.

U.S. Pat. No. 5,619,804 is directed toward an anatomical tape measuring reel with a window indicator to display the length measured.

U.S. Pat. No. 5,414,943 describes a manual anatomical measuring tape, with no take-up reel.

U.S. Pat. No. 5,588,428 describes a sophisticated computer-aided wound measuring apparatus based on laser technology.

It is possible, and indeed frequent practice, to measure wounds with a standard ruler, measuring tape, or other well-known simple devices displaying length demarcations.

However, such simple devices do not record details of size or physical appearance of the wound. Thus, medical personnel prefer to record details via the use of photography. But photographs of wounds often do not display the visual indicia used to measure the wound. Frequently these indicia are obscured, or too small to see.

Thus, there is a need in the medical industry for a wound calibration system that is easy to use, rapid in operation, and capable of being reliably recorded by photography for future diagnosis and treatment of the patient.

SUMMARY

An exemplary embodiment of the present invention is a wound calibration system that comprises elements of color, dimensioning, and optionally of photography.

The primary object of the invention is to provide a means for documenting accurate sizing of a wound on a patient in a hospital or other medical care environment.

Another object of the invention is to provide a means for recording wound size.

Another object of the invention is to provide a means for accurately recording wound size via the use of photography.

Another object of the invention is to provide a standardized color scheme across the medical care environment for measurement of wound sizes.

Another object of the invention is to provide a calibration scheme to facilitate the rapid and accurate sizing of a wound on a patient in a hospital or other medical care environment.

Yet another object of the invention is to provide a standardized color scheme for use in forensic investigations, such as at crime scenes.

Still another object of the invention is to provide a standardized color scheme for use in accident investigations, such as at vehicle or aircraft crash sites.

Other objects and advantages of the present invention will become apparent from the following descriptions, taken in connection with the accompanying drawings, wherein, by way of illustration and example, an embodiment of the present invention is disclosed.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as representative basis for teaching one skilled in the art to employ the present invention in virtually any appropriately detailed system, structure or manner.

Figure 1:
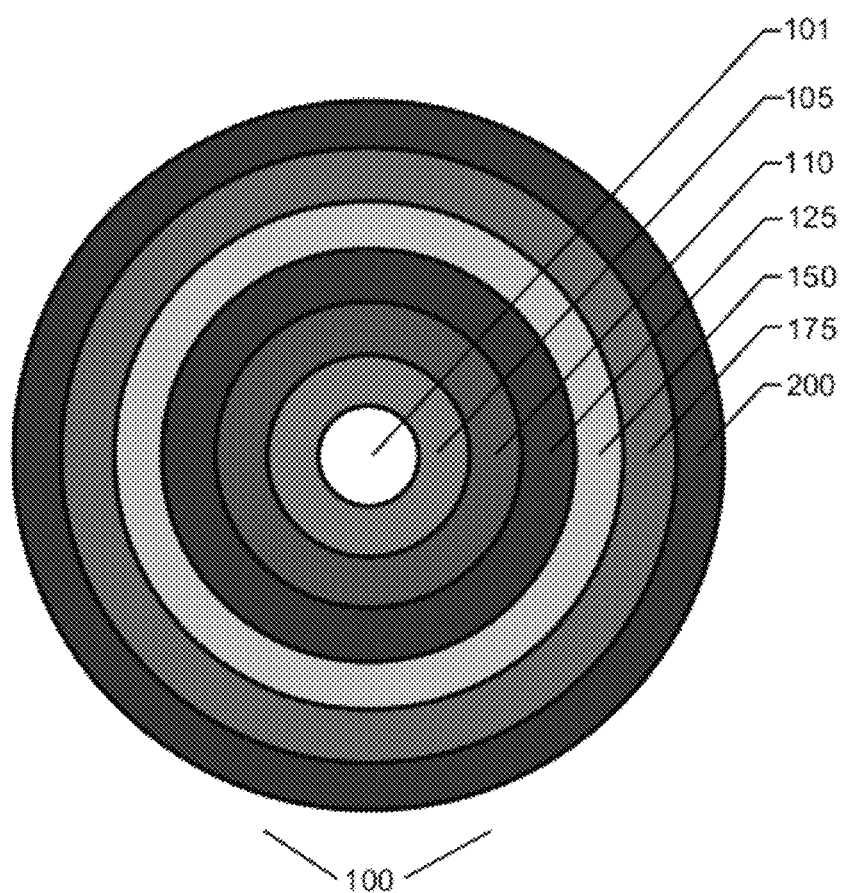
FIG. 1 is a plan view of a preferred embodiment of the current invention. The different shades of each ring are meant to indicate distinctive colors.

Referring now to FIG. 1 we see a preferred embodiment of the present invention. This embodiment 100 has an inner aperture 101, and concentric rings extending outward there from. The rings, in order from smaller inward-most to larger outermost, are: Ring 105, the smallest ring, with an inner area of 5 square centimeters; ring 110, the second smallest ring, with an inner area of 10 square centimeters; ring 125, the 3rd smallest ring, with an inner area of 25 square centimeters; ring 150, the next larger ring, with an inner area of 50 square centimeters; ring 175, the second largest ring, with an inner area of 75 square centimeters; and finally, ring 200, the largest ring, with an inner area of 100 square centimeters. Each ring is encoded with a label or other visual indicia indicating the size of its inner area.

The rings are also color-coded. From innermost ring, the color scheme number 1 currently provided is: ring 105, orange; ring 110, green; ring 125, blue; ring 150, yellow; ring 175, turquoise; and finally, ring 200, red.

The rings are used as a quick measure of the size of a wound on a patient. The operating assistant places the ring set just above the wound, and sequentially removes rings from the set, one at a time, from inward to outward, i.e. smallest to largest. After each ring removal, the operator views the wound through the central aperture. At the stage where sufficient rings have been removed to produce an aperture encompassing the entire wound, the operator stops and notes the size of the smallest remaining ring from its label or other indicia. This denotes the approximate wound size. An alternate method of application of the current invention is to remove one ring from the label and use the ring to photograph an accurate description of the wound.

Adhesive tabs corresponding to the color of the ring used can be applied to the medical chart as to reference the color. The size can also be embossed onto the tab.

A hospital is required to photograph the wound of a patient. This photograph is utilized to facilitate medical treatment and document the increase or decrease of the wound size. Observations have shown that the visual indicia tend to be too small to photograph effectively. Thus, a standardized color scheme allows for the photograph to record the wound size without reference directly to the visual indicia. The technician first arranges the rings in place around the wound. The photographer then takes color photographs. The photographs will record the wound appearance and size, through reference to the color of the rings.

Table I shows a color scheme and calibration size for a wound calibration system according to the current invention. If a color scheme, such as this one (though another will do as well—color scheme is arbitrary), is employed in standardized fashion, medical personnel can easily review photographs of the current invention in use and, from the color alone, determine wound size. Personnel can also refer to a chart, such as the one shown in Table I.

TABLE I

Ratings of wound size calibrated by the Present Invention color code

| Sq cm | Cm lineal | Color |
|---|---|---|
| 5 | 5 | Yellow |
| 10 | 10 | Blue |
| 15 | 15 | Orange |
| 20 | 20 | Magenta |
| 25 | 25 | Green |
| 50 | 50 | Purple |
| 75 | 75 | Cyan |
| 100 | 100 | Lime |

Figure 2:
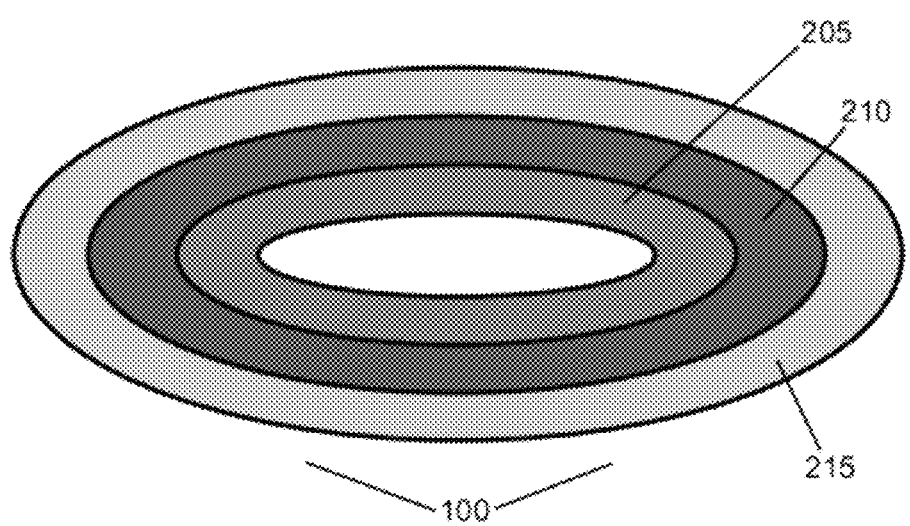
FIG. 2 is a perspective view of a simplified embodiment of the present invention, with fewer rings and different shape.

FIG. 2 shows a slightly different embodiment of a simplified form. This embodiment encompasses only 3 rings: ring 205, ring 210, and ring 215. By enlarging the width of the rings, this embodiment could be of coarser precision. For instance, ring 205 might define a width of 5 square centimeters within its inner border, while ring 210 may be as large as 25 cm, and ring 215 up to 75 cm. This might be useful in fast, approximate resolution of wound size, where speed is more important than precision and accuracy. The rings should be color coded according to a standardized scheme, so that, in the scheme of Table I, these rings would be colored as follows: ring 205, orange; 210, blue; and ring 215, cyan.

The ring set in one embodiment has adhesive backing, and thus forms a type of tape or label. It may be desirable to facilitate photography. The rings will later be removed. The rings are disposable to prevent the spread of infection from patient to patient.

Whether through the use of adhesive or other means, it is important in most embodiments of the current invention to design the rings such that they stay attached, in close contact with one another, until the inner ring or rings are removed during calibration and measurement. In one embodiment, the rings are prepared in a stack, such as for note pads. Adhesive is used to connect the rings to each other within a set, and to connect sets together in a stacked pad, from which each set is removed as needed for use. This method is equally effective for bars, or other shapes as employed in the current invention.

Figure 7:
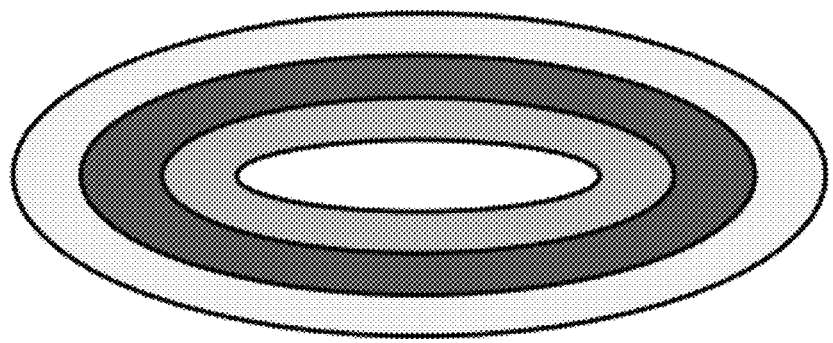
FIG. 7 shows another embodiment of the present invention utilizing ellipses.
Figure 8:
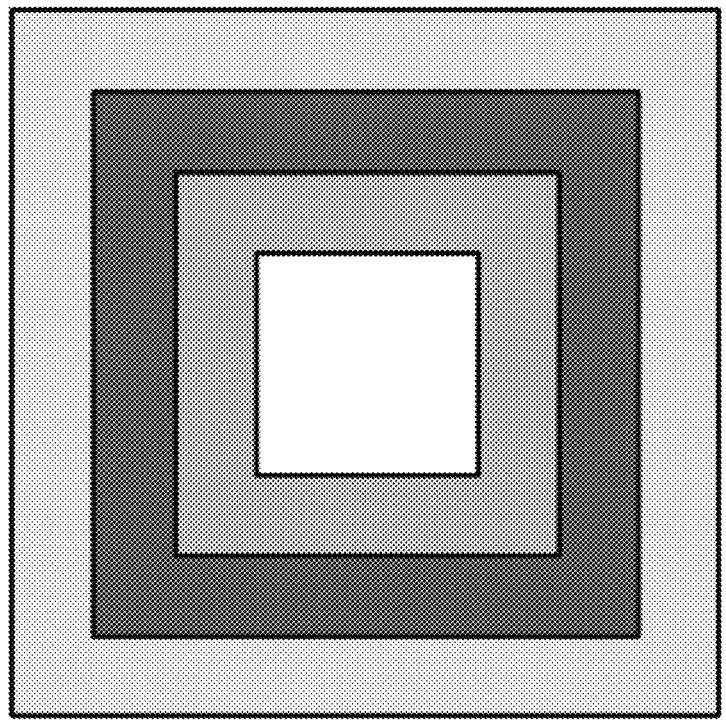
FIG. 8 shows a further embodiment utilizing squares.

It is important to note that the present invention contemplates other geometric shapes aside from circles. Concentric polygons of any closed shape could be used. Examples are nested triangles, squares, pentagons, hexagons, and octagons. FIGS. 7 and 8 shows respective embodiments utilizing elliptical and square shapes, for example. Other geometric shapes or irregular shapes are possible for use as well. Circles or rings are preferred, for a circle has a constant radius at all points around the circumference of the circle. This simplifies interpretation of photographs.

Figure 3:
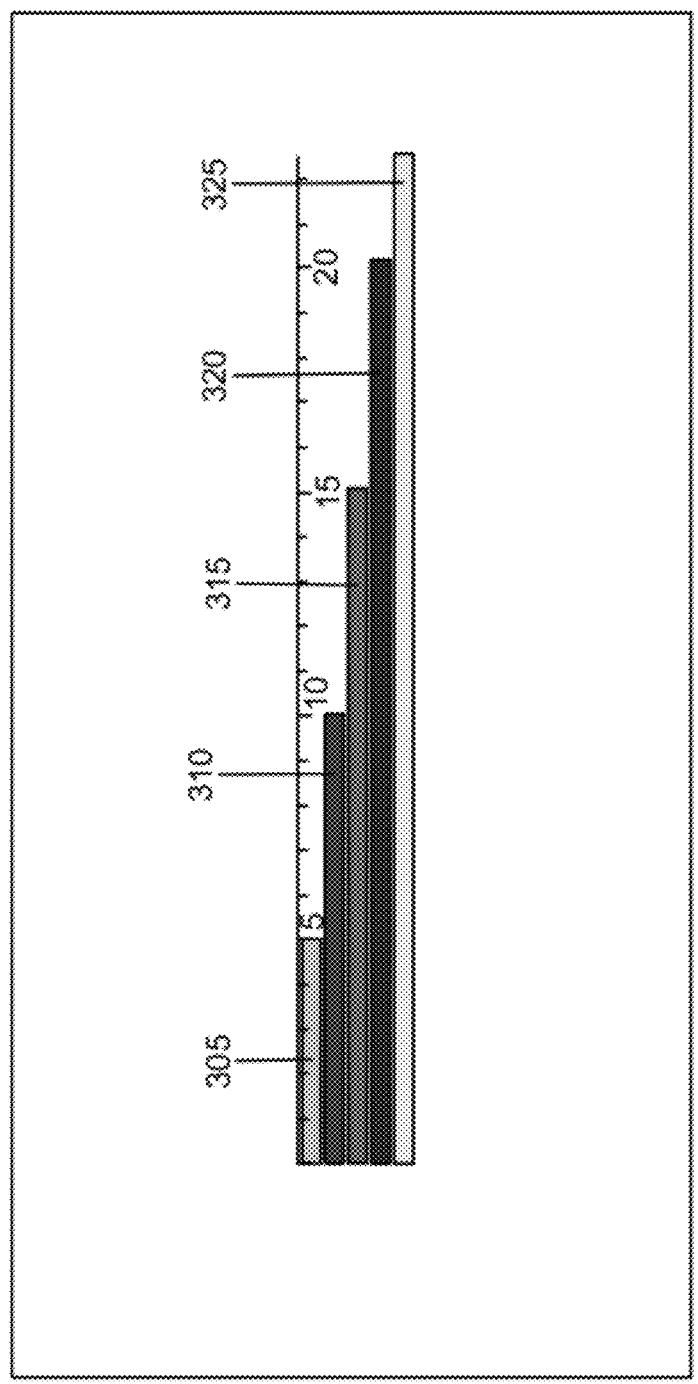
FIG. 3 is a plan view of a lineal embodiment of the present invention.

FIG. 3 illustrates an alternative form of the current invention. This embodiment is designed to measure the length of an irregular or linear wound. In this embodiment, the colored bars represent different lengths displayed with numeric ruler indicia. The bars are arranged side by side, as part of a flexible label. The bars can also be embodied as a rigid or semi-rigid composition, tape, or mounted on a transparent solid surface. FIG. 3 illustrates the bars as a label.

This embodiment can be even more simply and efficiently used than the area-calibrating rings. The operator simply applies the color bar ruler label next to the wound, and reads the ruler measurement of the wound. The bar ruler label can be applied to the patient using the adhesive that is optionally incorporated onto the backs of the bars. The colored bars next to each other offer an incremental reference for sizing. Photography may be employed as well, as described above. The color bar ruler label is held close to the wound at the point of the bar closest in length to the wound. Alternatively, all bars except the closest in length to the wound can be removed from the set, leaving only the single bar for the photograph. Also the bar ruler label can be trimmed with scissors so that it is scaled to the size of the wound.

Although the bars are useful in visual calibration, they are essential in the photographic record, for the numerical indicia of the ruler often do not record on the camera as well as do the colors.

In the example displayed in FIG. 3, the yellow bar 305 is on top, and represents a length of 5 centimeters. Lower bars 310, 315, 320, 325 of different colors extend to 10, 15, 20, and 25 cm. The chart of Table 1 provides the details.

It will be noted that the color code displayed for the bars in the wound size length calibration system of FIG. 3 is the same as the color code displayed for the rings in Table I. Ideally, the color scheme will be the same for both, as it reduces the possibility of confusion or error in the measurement and calibration process.

However, it is certainly possible within the contemplation of the current invention to have different color schemes for linear measurement, as in bars, as distinct from area measurement, as in rings. Indeed, in alternative embodiments of the current invention, colors need not be used. Each ring need only be visually distinct from each other ring, and the same for the bars. This could be accomplished by shading, cross-hatching or other drawing techniques, or use of additional visual indicia.

We make the above point so as to reinforce two important points of the present invention. First, the color code scheme is not important in and of itself. The color red, for instance, could represent a shorter length wound, or a longer one. Red could represent a small area wound, or a larger one. The importance is in the standardization of a scheme, such that red always means the same length bar, or inner area circle or polygon. Second, the linear dimension calibration of the bars is not the same (though related) dimension as the Table I rings provide. Nevertheless, color can and will be standardized and coordinated between the rings and bars, example being the red bar can have a value of 5 linear centimeters and the red ring represents 5 sq cm.

Figure 5:
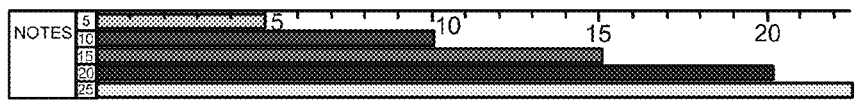
FIG. 5 is a plan view of a lineal embodiment of the present invention, with notation area depicted.

The rings or bars are preferably distributed as sets, mounted on a pad. In some embodiments, there is extra room on each sheet of the pad for writing notes, as displayed in FIG. 5, item 300. This could be valuable, for instance in dating the calibration, or making some other notes to be used in subsequent medical diagnosis. There may also be pull tabs on the bars, at the left of the zero point. Pull tabs are useful in that they carry the information of the length of the wound. The tabs are adhesive, and can easily be applied to paper surface, such as a patient's chart. This preserves useful and important information correlating to the patient's wound.

Figure 4:
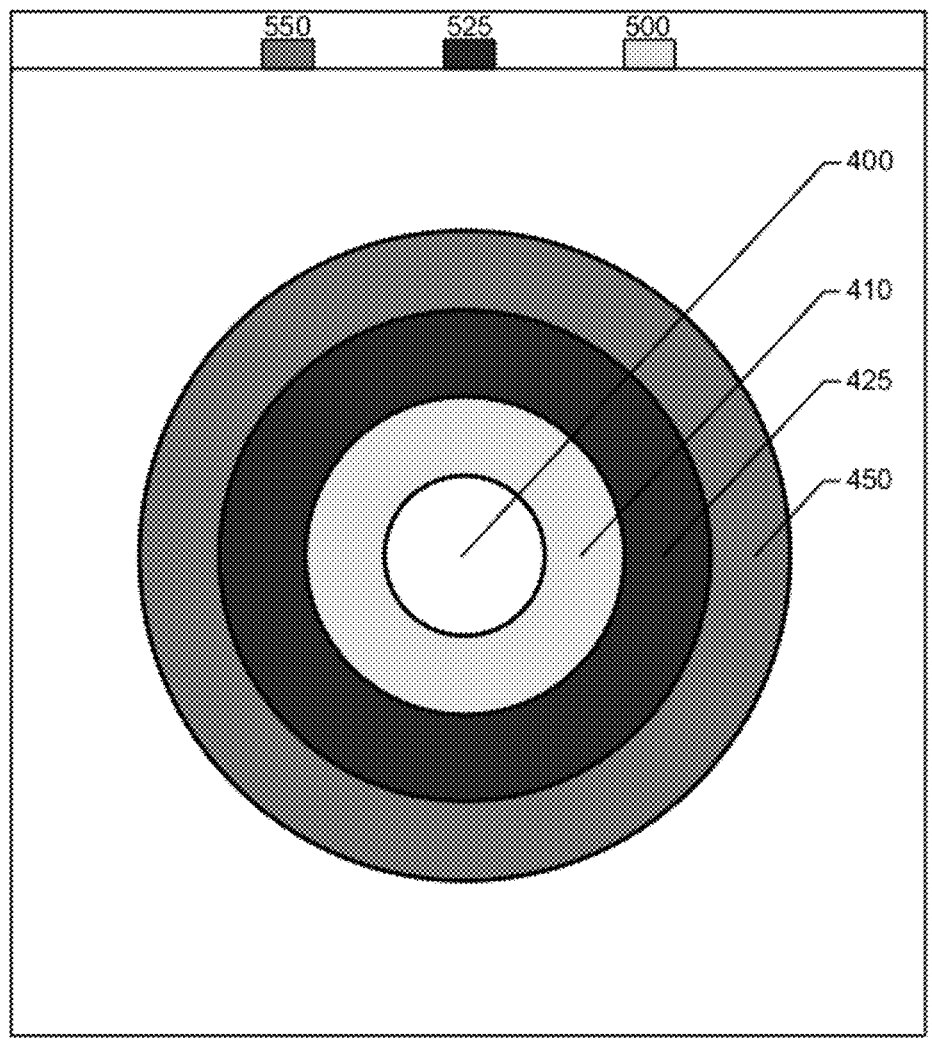
FIG. 4 shows another view of a simplified embodiment of the present invention, including the pull away colored tabs to attach to the medical chart to reflect the size of the ring used.

Similar pull tabs associated with rings are found in FIG. 4 where pull tab 550 corresponds to ring 450; tab 525 corresponds to ring 425; and tab 500 corresponds to ring 410. The pull tab shares the same color as the corresponding ring. Thus, if ring 425 is green, indicating a 25 sq cm wound area, as per Table 1, the corresponding pull tab 525 comprises the same color green.

Figure 6:
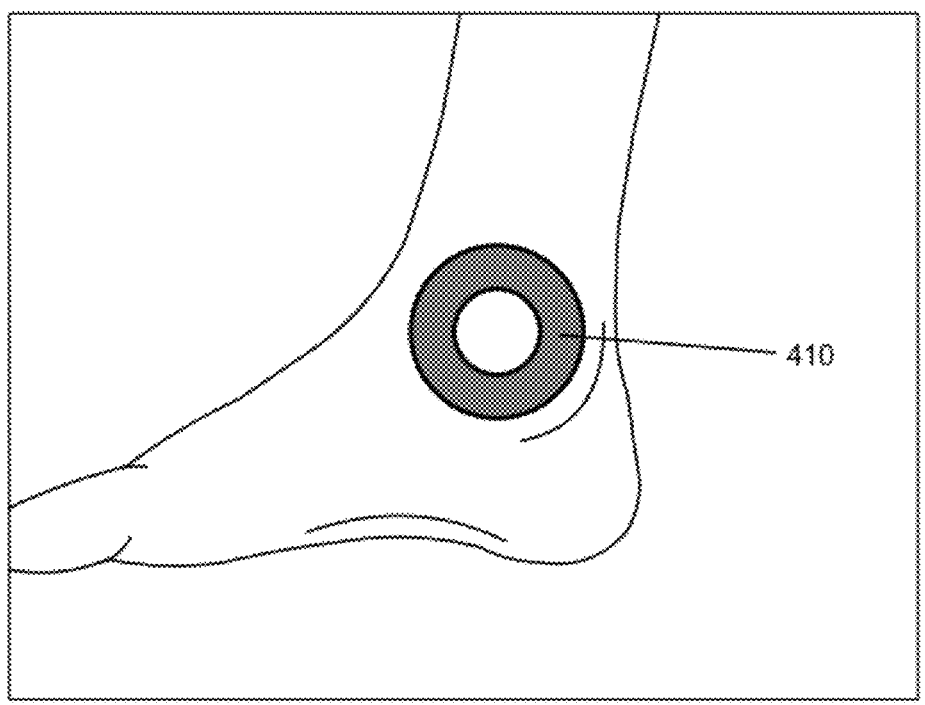
FIG. 6 shows the use of a ring of the current invention to highlight a wound on the ankle of a person.

FIG. 6 indicates the use of the present invention. In this figure, the injured area on the ankle is approximately 10 sq cm in area, and is so measured in FIG. 6 by the 10 sq cm ring, 410. The photograph is taken to record the wound, its measured size, and appearance. A pull tab could also go into the patient's file, indicating a 10 sq cm wound area.

The uses of the present invention are not limited to the medical field. Forensic investigators will also find the invention useful. For instance, crime scene investigators could measure wounds, scars, or markings on bodies, or on other surfaces through the use of the rings or bars of the current invention. Photographs could be taken, and the information recorded for subsequent study. Investigators in accident investigations could make similar use of the present invention, for example to calibrate areas at a crash site.

While the invention has been described in connection with a preferred embodiment or embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A device for visual indication of a size characteristic of an object, the device comprising:
a closed or linear device configuration having an actual size corresponding to one predetermined size characteristic value:
said device having a visual indicator representing said predetermined size characteristic value according to a predetermined visual indicator code scheme representative of a plurality of different size characteristic values;
said device having an adhesive backing configured to removably attach said device to a backing sheet and for removal from the backing sheet for application of the device to the object;
wherein said device actual size is a length or area characteristic; and
wherein the device visual indicator is a color indicating said size characteristic value, and said code scheme includes a plurality of different colors each identifying a different size characteristic value in a color code scheme and calibration size table to facilitate color photography of the object with the applied device.

2. The device of claim 1, wherein said device has a closed configuration surrounding a predetermined open area indicated by said visual indicator.

3. The device of claim 2 wherein said device is a ring circumscribing said predetermined open area.

4. The device of claim 3, wherein the object is a wound, and the ring is adapted to surround a wound.

5. The device of claim 1, wherein said configuration is a linear bar configuration comprising a length of a predetermined length.

6. The device of claim 1, wherein said device further comprises a removable pull tab containing indicia indicating said length or area characteristic associated with said device.

7. A method for calibrating and measuring a size characteristic of an object, comprising:
providing a calibration device having a closed or linear device configuration, the device having an actual size corresponding to one predetermined size characteristic value, said device having a visual indicator representing said predetermined size characteristic value according to a predetermined visual indicator code scheme representative of a plurality of different size characteristic values, wherein said device actual size is a length or area characteristic, and wherein the device visual indicator is a color indicating said size characteristic value, and said code scheme includes a plurality of different colors each identifying a particular size characteristic;
arranging said device around or alongside the object; and
recording a color image of the device and the object, and wherein the image reflects said color and thereby indicates said size characteristic in relation to the object, wherein recording said image comprises:
recording the color image with a camera; and
producing a photograph or electronic image for future use.

8. The method of claim 7, wherein said device has a closed configuration surrounding a predetermined open area indicated by said color.

9. The method of claim 7 wherein said device is a ring circumscribing said predetermined open area.

10. The method of claim 9, wherein the object is a wound on a patient's body, and said step of arranging said device around or alongside the wound comprises arranging the ring to surround the wound.

11. The method of claim 7, wherein said configuration is a linear bar configuration of a predetermined length.

12. The method of claim 7, wherein said device further comprises a removable pull tab containing indicia indicating said length or area characteristic associated with said device.

13. A calibration and measurement system for visual indication of a size characteristic of an object or a wound on a patient, the system comprising:

a set of closed or linear measurement devices each device indicative of a size characteristic associated with the device and configured for application to the object or patient;

each device of said set being visually distinct from each other device, wherein the devices are colored, and each device is a different color from each other device;

each device having a length or area characteristic which is different from a length or area characteristic of each other device of said set, wherein each different color represents an associated size or length characteristic according to a predetermined color code scheme representative of a plurality of different size or length characteristic values;

wherein each device of said set is removably mounted to one sheet and removable relative to other devices of said set, and said set is so configured as to allow selective removal of an individual device from the sheet for application to the object or patient without removing the remaining devices of said set from the sheet.

14. The system of claim 13, wherein said set of devices is a set of closed devices, and each device surrounds a predetermined open area which is different from the predetermined area surrounded by each other device of said set.

15. The system of claim 14, wherein each device of the set of closed devices is removably mounted in a concentric relationship.

16. The system of claim 14, wherein said set of closed devices is a set of closed polygon devices each circumscribing an open area of a different area from each other device of said set.

17. The system of claim 13, wherein said devices of said set are constructed of paper or synthetic material.

18. The system of claim 13, wherein said set of devices comprises:
a planar set of linear bars, arranged in side-by-side order;
each bar comprising a length of known dimensions, and different from the length of each other bar.

19. The system of claim 13 wherein said devices have an adhesive backing.

* * * * *